United States Patent
Koivusalmi

(10) Patent No.: US 7,795,484 B2
(45) Date of Patent: Sep. 14, 2010

(54) PROCESS FOR THE MANUFACTURE OF BASE OIL

(75) Inventor: Eija Koivusalmi, Kulloonkylä (FI)

(73) Assignee: Neste Oil Oyj, Espoo (FI)

( * ) Notice: Subject to any disclaimer, the term of this patent is extended or adjusted under 35 U.S.C. 154(b) by 571 days.

(21) Appl. No.: 11/812,041

(22) Filed: Jun. 14, 2007

(65) Prior Publication Data

US 2007/0299291 A1    Dec. 27, 2007

Related U.S. Application Data

(60) Provisional application No. 60/813,368, filed on Jun. 14, 2006.

(51) Int. Cl.
*C07C 1/213* (2006.01)
*C07C 1/24* (2006.01)

(52) U.S. Cl. .................. 585/324; 585/326; 585/327; 585/329

(58) Field of Classification Search ............ 585/324, 585/326, 327, 329
See application file for complete search history.

(56) References Cited

U.S. PATENT DOCUMENTS

| | | | |
|---|---|---|---|
| 3,322,848 A | 5/1967 | Garwood et al. | |
| 4,218,330 A | 8/1980 | Shubkin | |
| 4,386,229 A | 5/1983 | Heckelsberg et al. | |
| 4,554,397 A | 11/1985 | Stern et al. | |
| 4,967,032 A | 10/1990 | Ho et al. | |
| 5,453,556 A | 9/1995 | Chang et al. | |
| 5,597,944 A | 1/1997 | O'Young et al. | |
| 5,608,122 A | 3/1997 | Buchold et al. | |
| 5,714,661 A | 2/1998 | Tuli et al. | |
| 6,204,424 B1 | 3/2001 | Yadav et al. | |
| 6,683,224 B1 | 1/2004 | Hourticolon et al. | |
| 6,703,356 B1 | 3/2004 | Wu | |
| 2004/0249229 A1 | 12/2004 | Gee et al. | |
| 2006/0182681 A1 | 8/2006 | Kumar et al. | |

FOREIGN PATENT DOCUMENTS

| | | |
|---|---|---|
| DE | 3915493 A1 | 11/1990 |
| WO | WO-01/44145 A1 | 6/2001 |
| WO | WO 2004/078336 A2 | 9/2004 |

OTHER PUBLICATIONS

Hayes PC et al., Journal of Chromatography 253 (1982), pp. 179-198.
Wagner et al., Applied Catalysis A: General 221 (2001), pp. 429-442.
Petrov et al., Zhurnal Obshchei Khimii (Journal of General Chemistry), vol. 18, pp. 859-864, 1948.

*Primary Examiner*—Thuan Dinh Dang
(74) *Attorney, Agent, or Firm*—Birch, Stewart, Kolasch & Birch, LLP

(57) ABSTRACT

A feedstock originating from renewable sources is converted to branched and saturated hydrocarbons without heteroatoms in the base oils distillation range by converting the fatty acids to olefins, which are subsequently oligomerised.

18 Claims, 1 Drawing Sheet

PROCESS FOR THE MANUFACTURE OF BASE OIL

Figure 1:
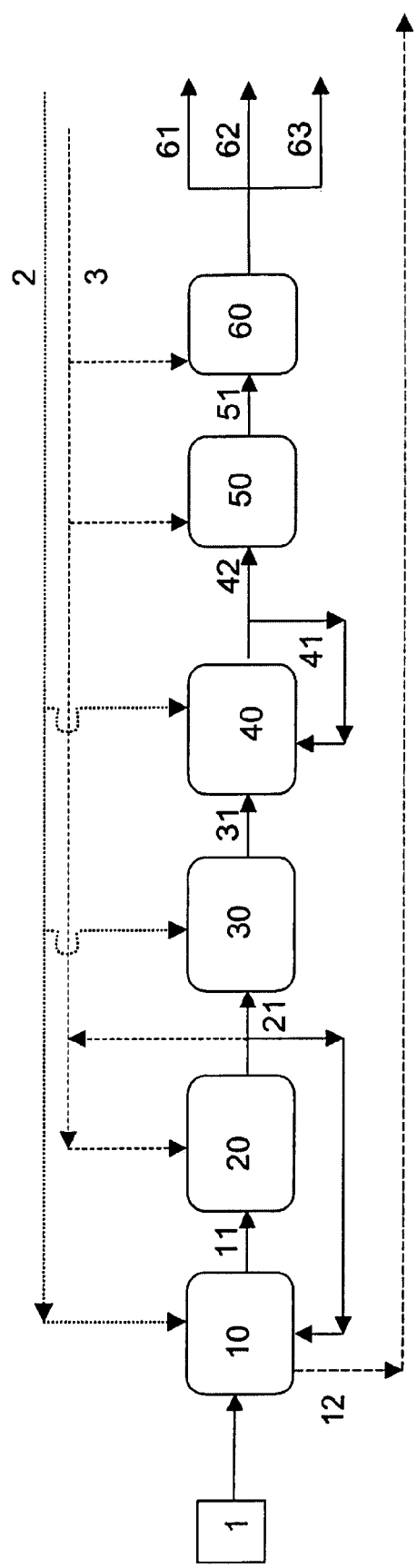

This Nonprovisional application claims priority under 35 U.S.C. §119(e) on U.S. Provisional Application No(s). 60/813,368 filed on Jun. 14, 2006, the entire contents of which are hereby incorporated by reference.

FIELD OF THE INVENTION

The present invention relates to a process for the manufacture of hydrocarbons, particularly for the manufacture of branched saturated hydrocarbons from renewable sources, and to a process for the manufacture of hydrocarbons suitable for base oil and particularly polyalpha-olefins. The process comprises an olefin preparation step, followed by an olefin oligomerisation step and a hydrogenation step.

BACKGROUND OF THE INVENTION

Base oils are used for the manufacture of lubricating oils for automobiles, such as engine oils and transmission oils, and for industrial uses, such as greases, process oils, white oils, and metal working oils. Lubricants are base oil formulations containing typically additives to enhance their properties for specific applications. Among the more commonly used additives in lubricant formulations are oxidation inhibitors, rust inhibitors, metal passivators, anti-wear agents, extreme pressure additives, pour point depressants, detergent-dispersants, viscosity index improvers, foam inhibitors and the like. Base oil is the major constituent in lubricant products and contributes significantly to the properties of the finished lubricant product.

Efforts to improve the performance of lubricants by providing hydrocarbon base oils with improved technical properties have been the subject of research and development work in the petroleum industry for several years. This is because new engine technologies require more robust lubricants than those based on conventional mineral oils. In terms of lubricant and thus base oil property improvement, industrial research has been toward fluids exhibiting useful viscosities over a wider range of temperature, i.e., improved viscosity index (VI), while also showing lubricity, thermal and oxidative stability and pour point equal to or better than mineral oil. These synthetic lubricants exhibit lower friction characteristics and they are therefore capable of increasing mechanical efficiency of various types of equipment including engines, transmissions, worm gears and traction drives, over a wider range of operating conditions than conventional mineral oil lubricants.

In addition to engine technology, also strict environmental requirements direct the industry to develop more sophisticated base oils. Sulphur free fuels and base oils are required in order to gain full effect of new and efficient anti-pollution technologies in modern vehicles and to cut emissions of nitrogen oxides, volatile hydrocarbons and particles, as well as to achieve direct reduction of sulphur dioxide in exhaust gases. The European Union has decreed that these fuels shall be available to the market from 2005 and they must be the only form on sale from 2009. Conventional mineral oil base oils contain sulphur, nitrogen, aromatic compounds, and typically also volatile compounds. They are less suitable for the new engines and thus also environmentally more detrimental than newer no-sulphur, no-aromatic base oils.

It can be assumed that the use of base oils, which are based on biological raw materials, will result in a significant reduction in carbon dioxide emissions. This is due to the closed carbon cycle of the renewable base oil. The $CO_2$ released into the atmosphere when burning the base oil at the end of their lifecycle or due to oil loss by burning within the engine, is recycled by growing plants, which are later processed into base oil. As such, the increased use of base oils, which are based on biological material, represents an important step to meet the emission reduction target as agreed under the Kyoto agreement.

The increasing demand for high performance lubricants particularly requires high quality base oils. The American Petroleum Institute (API) classifies base oils according to the characteristics shown in Table 1. A similar classification is used also by the Association Technique de L'Industrie Européenne des Lubrifiants (or Technical Association of The European Lubricants Industry, ATIEL), containing also Group VI, polyinternalolefins (PIO). In the classification, the term "saturates" includes both paraffinic and naphthenic compounds but not aromatic compounds.

API 1509 defines a base stock as: "A base stock is a lubricant component that is produced by a single manufacturer to the same specifications (independent of feed source or manufacturer's location); that meets the same manufacturer's specification; and that is identified by a unique formula, product identification number, or both. Base stocks may be manufactured using a variety of different processes including but not limited to distillation, solvent refining, hydrogen processing, oligomerization, esterification, and rerefining. Rerefined stock shall be substantially free from materials introduced through manufacturing, contamination, or previous use." Base oil is the base stock or blend of base stocks used in API-licensed oil.

Generally lubricating base oils are base oils having kinematic viscosity of about 3 $mm^2/s$ or greater at 100° C. (KV100, kinematic viscosity measured at 100° C.); a pour point (PP) of about −12° C. or less; and a viscosity index (VI) about 120 or greater. The oils in Group III are very high viscosity index (VHVI) base oils, which are manufactured from crude oil by hydrocracking and catalytic dewaxing or solvent dewaxing. Group III base oils can also be manufactured by catalytic dewaxing of slack waxes originating from crude oil refining, or by catalytic dewaxing of waxes originating from Fischer-Tropsch synthesis from natural gas or coal based raw materials. Group IV base oils are polyalphaolefin (PAO) base oils.

TABLE 1

| API-classification of base oils | | | |
|---|---|---|---|
| Group | Saturates/wt-% (ASTM D 007) | Sulphur/wt-% (ASTM D 1552/D 2622/D 3120/D 4294/D 4927) | Viscosity index (VI) (ASTM D 2270) |
| I | <90 and/or | >0.03 | 80 ≦ VI < 120 |
| II | ≧90 | ≦0.03 | 80 ≦ VI < 120 |
| III | ≧90 | ≦0.03 | 120 ≦ VI |
| IV | All polyalpha-olefins (PAO) | | |
| V | All other base oils not included in Groups I-IV | | |

Fatty acids have been used as raw materials in various applications in chemical industry, typically in the manufacture of products ranging from lubricants, polymers, fuels and solvents to cosmetics. Fatty acids are generally obtained from wood pulping processes or by hydrolysis of triglycerides of vegetable or animal origin. Naturally occurring triglycerides are usually esters of glycerol and straight chain even numbered carboxylic acids having 10-26 carbon atoms. Most common fatty acids contain 16, 18, 20 or 22 carbon atoms. Fatty acids may either be saturated or they may contain one or more unsaturated bonds. Unsaturated fatty acids are often olefinic having carbon-carbon double bonds with cis configuration. The unsaturated centers appear in preferred positions in the carbon chain. The most common position is ω9, like in oleic acid (C18:1) and erucic acid (C22:1). Polyunsaturated acids generally have a methylene-interrupted arrangement of cis-olefinic double bonds.

Conventional base oils of biological origin comprise esters and their use is limited to specific applications, such as refrigeration compressor lubricants, bio-hydraulic oils and metal working oils. As polar compounds, esters suffer greater seal-swelling tendency than hydrocarbons when used as engine oils. In hydraulic applications, esters are not suitable for use together with hose elastomers. In addition, the esters used in engine oil formulations are not interchangeable with other esters without performing new engine tests. Instead, base oils consisting of pure hydrocarbon structure are partly interchangeable with each other. Ester base oils are hydrolyzed easily producing acids, corroding lubricating systems when used as engine oils. Further, even greater disadvantage of esters is that additives developed for non-polar hydrocarbon base oils are not effective for ester base oils. A further major disadvantage of synthetic esters is that they are inherently more expensive than high quality mineral base oils.

The need of high quality base oils has led to the introduction of a number of polyalpha-olefin based synthetic lubricants produced by oligomerization of alpha-olefins (1-alkenes). Polyalpha-olefins, useful as synthetic base oils may be synthesized by homogeneous Friedel-Crafts catalyst such as $BF_3$ or $AlCl_3$, typically followed by hydrogenation to stabilize the oligomer against oxidation and degradation. In a typical polyalpha-olefin production process, 1-decene is used as the starting material. Polymers of 1-decene and mixtures of 1-decene with 1-octene and/or 1-dodecene generally result in base oils having a high viscosity index (VI) and low pour point. Polyalpha-olefins are useful as base oils for lubricants, transmission fluids, and transformer fluids.

Typically highly saturated polyalpha-olefin base oils contain very low levels of cycloparaffins and highly saturated VHVI base oils contain high levels of multicycloparaffins. A certain amount of monocycloparaffins is desired in base oils to provide adequate additive solubility and elastomer compability. Multicycloparaffins are less desirable than monocycloparaffins due to their poorer viscosity index, lower oxidation stability, and increased Noack volatility.

Olefins having from about 5 to about 20 carbon atoms are prepared by a number of methods including thermal and catalytic cracking of petroleum fractions, thermal cracking of paraffin wax, dehydrochlorination of monochlorinated paraffinic hydrocarbons, polymerization of low molecular weight olefins by the Ziegler process, hydrogenation of fatty acids to alcohols with subsequent dehydration of alcohols to olefins, and hydrogenation of fatty acid esters or triglycerides to paraffins with subsequent dehydrogenation of paraffins to olefins.

Fatty alcohols can be produced on commercial scale by hydrogenolysis, or in other words by hydrogenation of fatty esters, fatty acids or triglycerides. In the fatty ester route, the preparation of an intermediate methyl ester or wax ester product is used. U.S. Pat. No. 5,608,122 discloses a process for preparing wax esters (or fatty esters) and subsequent hydrogenation of wax esters to fatty alcohols. In the esterification step, fatty acids and fatty alcohols are esterified at a temperature of 120-320° C. in the excess of circulating fatty alcohol without catalyst. The intermediate wax ester product is hydrogenated at 100-300° C. under a pressure of 20-40 MPa using conventional copper-chromite or copper catalysts to produce fatty alcohol.

Direct hydrogenation of fatty acids to produce fatty alcohols is not that widely used due to need of higher reaction temperatures resulting in lower yields, and due to damaging effects of fatty acids on the catalyst. In direct hydrogenation process of triglycerides to fatty alcohols, in addition to fatty alcohols and glycerol also propane diol and propanol are obtained as the over-reduction products of glycerol. U.S. Pat. No. 6,683,224 teaches a process for the continuous production of fatty alcohols by the hydrogenation of naturally occurring fats, oils and fatty derivatives in a fixed-bed reactor at a temperature 160-320° C. under a pressure of 5-30 MPa in the presence of at least stoichiometric amount of hydrogen. In the process both the ester groups and also carbon double bonds are hydrogenated on the copper-containing catalyst to form saturated fatty alcohols, even in cases where unsaturated esters are used as feedstock.

Dehydration of alcohols to form olefins is one of the oldest catalytic reactions, and numerous oxides are suitable catalysts for this reaction. Activated alumina is the primary industrial catalyst, typical conditions being atmospheric pressure, temperature of 250-400° C. and 1-5 m$^3$ of liquid per h/m$^3$ of catalyst. DE 3,915,493 discloses a process for dehydration of fatty alcohols under normal pressure and at a temperature of 280-300° C. in vapor phase. WO 01/44145 describes a dehydration process to convert C4-C40 alcohols to olefins by a zirconium oxide on aluminium oxide catalyst.

U.S. Pat. No. 4,554,397 discloses a process for the manufacture of linear olefins from saturated fatty acids or esters by decarboxylation, using a catalytic system consisting of nickel and at least one metal selected from the group consisting of lead, tin and germanium. Additives may be included in the above-mentioned catalysts and for example sulphur derivatives may be added to decrease the hydrogenating power of nickel and to improve the selectivity for olefin formation reaction. The presence of hydrogen is necessary to maintain the activity of the catalyst. The reaction is carried out at a temperature of 300-380° C. and the pressure is atmospheric pressure or higher. This reaction is applicable particularly to saturated linear carboxylic acids having from 6 to 30 carbon atoms, as well as to esters formed form said acids and mono- or polyhydric alcohol.

U.S. Pat. No. 5,597,944 discloses a process for producing n-olefins via dehydrogenation of C5 to about C20 n-paraffins by dehydrogenating in the presence of manganese oxide octahedral molecular sieve as catalyst. The presence of hydrogen is necessary to prevent coking of the catalyst. Reaction temperatures for the catalytic dehydrogenation of n-paraffin hydrocarbons range from about 100° C. to about 750° C. Since the dehydrogenation reaction is endothermic, heat must be continually added to the reaction in order to maintain the reaction.

A conventional route to prepare 1-decene and other linear alpha-olefins is via oligomerisation of ethylene using an alkylated metal catalyst, also resulting in a wide spectrum of products having even-numbered carbon chain lengths. Polymerization of ethylene usually produces a wide range of alpha-olefins, from 1-butene to 1-C20 and higher alpha-olefins, with the product distribution governed by the degree of polymerization. The higher alpha-olefins, such as C14 or higher, generally are not used as starting materials for polyalpha-olefin production because the resulting polymers typically have undesirable properties such as high pour point and high volatility that render them unsuitable for use as high performance base oils.

U.S. Pat. No. 4,218,330 presents a process for oligomerising higher olefins such as C12-C18 with homogeneous cationic catalysts, such as boron trifluoride, to form lubricant products. Polyalpha-olefin processes using homogeneous catalysts always include a complicated and tedious catalyst separation step.

U.S. Pat. No. 3,322,848 discloses a method of manufacturing lubricating oils from C10-C18 alpha-olefins using a microporous catalytic agent prepared by base exchanging a crystalline alkali metal aluminosilicate having uniform pore openings of 6 to 15 Ångström units with an ionisable metal compound, such as rare earth metals. This process generally resulted in low lube yields and significant amounts of coke formation. Furthermore, the products made from 1-dodecene or 1-tetradecene had relatively high pour points.

U.S. Pat. No. 5,453,556 provides an oligomerisation process where a catalyst comprising an acidic solid comprising a Group IVB metal oxide, such as zirconia, modified with an oxyanion of a Group VIB metal, such as tungsten, is used. A C6-20 alpha-olefin feedstock is contacted with the oligomerisation catalyst under a reaction temperature between 20° C. to 250° C.

U.S. Pat. No. 6,703,356 discloses conversion of higher olefins using high activity crystalline zeolite catalysts with widely open structures and having high activity for polymerization. In addition, mixed oxide catalysts, such as $WO_x/ZrO_2$, and acid clay catalysts may also be used. The polyolefins produced in accordance with the processes have low viscosity, volatility, and pour point characteristics when compared to conventional polyalpha-olefins formed from C8-C12 olefins.

Based on the above, it can be seen that here is a need for a new alternative process for the preparation of saturated and branched hydrocarbons from renewable sources suitable as high quality base oil.

OBJECT OF THE INVENTION

An object of the invention is an alternative process for the manufacture of branched saturated hydrocarbons from renewable sources.

A further object of the invention is an alternative process for the manufacture of branched saturated hydrocarbons suitable for Group IV base oils.

A still further object of the invention is an alternative process for the manufacture of polyalpha-olefins.

A still further object of the invention is a polyalpha-olefin product obtainable by the process according to the invention.

Characteristic features of the process and polyalpha-olefin product according to the invention are provided in the claims.

SUMMARY OF THE INVENTION

The present invention relates to a process for the manufacture of branched saturated hydrocarbons, which are suitable for base oils or base oil components. In accordance with the present invention, a new alternative process has been discovered for producing polyalpha-olefins from olefins, and particularly from alpha-olefins obtained from higher fatty acids, such as C12 and higher. Olefins are used in this process as intermediates for oligomer manufacturing, thereby easing the demand for high price 1-decene and other crude oil or synthetic gas based olefins as feedstock. In a preferred embodiment, the process of the invention utilizes renewable raw materials for source of olefin production and heterogeneous acidic microporous or mesoporous catalysts to oligomerise these olefins. Suitably the feedstock comprises fatty acids obtained from renewable sources, such as plant, vegetable, animal and fish fats and oils. The resulting oligomers have excellent pour point, volatility and viscosity characteristics and additive solubility properties.

The process according to the invention comprises the steps where, in the first step, a feedstock comprising fatty acids is transformed to esters, in the second step the esters are transformed to fatty alcohols, in the third step the fatty alcohols in turn are converted to alpha-olefins, in the fourth step the obtained alpha-olefins are converted to branched hydrocarbons by contacting them either with a homogeneous or heterogeneous oligomerisation catalyst, and in the fifth step the obtained oligomers are hydrogenated to produce thermally stable base oils or base oil components.

A high quality hydrocarbon product with good low temperature properties and high viscosity index is obtained by employing feedstock comprising heteroatoms from biological origin.

A preferable embodiment of the process according to the invention is presented in appended FIG. 1.

FIG. 1

In FIG. 1 heated fatty acid feed 1 enters together with 1-2 molar excess of recycled fatty alcohol 21 to an esterification reactor 10 to form a wax ester 11. The reaction is carried out at about atmospheric pressure and 150-250° C. temperature without catalyst. Water 12 liberated in the reaction is emerged by spraying inert gas 2, such as nitrogen. The wax ester 11 and hydrogen 3 are charged to the hydrogenation reactor 20, where the esters are hydrogenated to fatty alcohols 21. The hydrogenation reaction is carried out at 20-30 MPa pressure and 150-250° C. temperature with copper-chromite catalyst. The reactor discharge product is cooled (not presented in the FIGURE) and separated into recycled hydrogen 3 and liquid crude fatty alcohol 21. Part of fatty alcohol 21 is directed to dehydration reactor 30 for processing to alpha-olefins 31 and part of fatty alcohol 21 is recycled to the esterification reactor 10. The dehydration reaction is carried out at about atmospheric pressure and 280-330° C. temperature with zirconium oxide on gamma-alumina catalyst. The alpha-olefins 31 are charged to the oligomerisation reactor 40, where they are oligomerised. The reaction is carried out under a pressure from about 0.01 to about 2 MPa and 50-200° C. temperature. The required pressure maybe maintained by inert gas 2 pressurization, preferably nitrogen. The catalysts in oligomerisation are preferably mesoporous materials, zeolites or mixtures thereof. Unreacted monomers 41 are removed from the oligomer mixture and recycled to the oligomerisation reactor 40. After removing of the monomers, the polyalpha-olefin mixture 42 is comprised of dimers, trimers, tetramers and other higher oligomers. The polyalpha-olefin mixture 42 and hydrogen 3 are charged to the hydrogenation reactor 50 and the polyalpha-olefin mixture 42 is hydrogenated in the presence of hydrogenation catalyst, such as palladium on carbon catalyst, or nickel on Kieselguhr catalyst. The reaction is carried out at a temperature of about 150-200° C. and hydrogen pressure of 1-3 MPa. The hydrogenated polyalpha-olefin product 51 is charged to the distillation unit 60 and it may be distilled to fractions consisting mainly dimers 61, trimers 62 and/or higher oligomers 63.

DEFINITIONS

Fatty acids mean carboxylic acids obtained from biological raw material. The carbon number of said fatty acids is higher than C1, preferably at least C4.

Saturated base oil or base oil component comprises saturated hydrocarbons. Saturated hydrocarbons comprise paraffinic and naphthenic compounds but no aromatics. Paraffinic compounds may be branched or linear compounds.

Naphthenic compounds are cyclic saturated hydrocarbons, also known as cycloparaffins. Naphthenic compounds may contain one ring structure (monocycloparaffins) or two rings (dicycloparaffins) or several rings (multicycloparaffins).

Olefins are defined herein as a class of unsaturated aliphatic hydrocarbons having one or more double bonds. These olefins may be straight chain olefins or branched chain olefins. The olefins may be alpha-olefins, internal olefins, vinylidene olefins, or mixtures thereof. The olefins manufactured according to the present invention are preferably alpha-olefins obtained from biological raw materials.

The width of carbon number range means here the difference between the carbon number of the biggest and the smallest molecule, added with one.

DETAILED DESCRIPTION OF THE INVENTION

It was surprisingly found that saturated and branched hydrocarbons, suitable as base oils or base oil components can be obtained from heteroatom containing feedstocks originating from renewable sources by structural reformation of the feedstock compounds to olefinic compounds, followed by oligomerisation.

A novel process is now provided producing saturated and branched polyalpha-olefin hydrocarbons originating from olefins obtained from fatty acids, preferably from higher fatty acids, such as at least C12 fatty acids. The feedstock is converted to olefins by decarboxylation, or hydrogenated to paraffins with subsequent dehydrogenation of the paraffin to the olefin. Preferably, feedstock is converted to fatty alcohols with chain length according to the carbon number of the fatty acid feedstock, and is further dehydrated to alpha-olefins. Preferably renewable raw materials of biological origin are used for source of olefin production. Alpha-olefins are oligomerised and hydrogenated to produce branched hydrocarbon base oils, wherein the oligomerisation of olefins is carried out in the presence of a homogeneous or heterogeneous oligomerisation catalyst. Preferably, heterogeneous acidic microporous or mesoporous catalysts are used. The resulting polyalpha-olefins have excellent pour point, volatility and viscosity characteristics and additive solubility properties.

The process according to the invention comprises the steps where, in the first step feedstock comprising at least one carboxylic acid, preferably fatty acid is esterified with at least one fatty alcohol, in the second step the obtained esters are hydrogenated to fatty alcohols, in the third step the fatty alcohols in turn are dehydrated to alpha-olefins, in the fourth step the obtained alpha-olefins are oligomerised to branched hydrocarbons by contacting them either with a homogeneous or heterogeneous oligomerisation catalyst, and in the fifth step the oligomers produced are hydrogenated to produce thermally stable base oils or base oil components, particularly polyalpha-olefins.

Feedstock

The feedstock comprises at least one fatty acid or a mixture of fatty acids. The feedstock preferably originates from biological raw materials such as plant, vegetable, animal and fish oils and fats, which also may originate from circulated and used food oils and fats and combinations thereof. The biological raw material may be treated using any pre-treatment or purification method well known in the art to obtain fatty acids useful as the feedstock, such as hydrolysis through high pressure fat splitting, distillation and fractionation.

Fatty acids useful as feedstock have a total carbon number of 8 to 26, preferably 12 to 20 and particularly preferably 12 to 18. Both saturated and unsaturated fatty acids may be used. These fatty acids may be straight chain or branched chain fatty acids. The oligomers may be made from a single fatty acid or from mixtures of two or more fatty acid. For example, C16 fatty acid by itself is a suitable starting material, as well as mixtures of C14, C16, C18, and/or C12 to C18 fatty acids in any proportion. Generally, dimers produced from the smallest fatty acids, having more than about 26 carbon atoms are preferred oligomerisation products and possess good volatility and viscosity characteristics. The carbon number of the dimer product is preferably between 16 and 52, particularly preferably between 26 and 50.

Process

The process according to the invention comprises five steps. In the first step of the process a feedstock comprising at least one fatty acid is heated and esterified together with 1-2 molar excess of recycled fatty alcohol having total carbon number of 8 to 26, preferably from 12 to 20, obtained from the subsequent hydrogenation step in a reactor system to form a wax ester. The esterification takes place under pressure of 0-0.1 MPa without a catalyst, at a temperature of 120-320° C., preferably 150-250° C. Water liberated in the esterification reaction is emerged by spraying inert gas, such as nitrogen.

In the second step the wax ester obtained in the first step is hydrogenated in a batch or fixed bed hydrogenation reactor in the presence of a catalyst selected from copper catalysts and copper-chromite catalysts and hydrogen at a temperature of 100-350° C., preferably 150-250° C. and under a pressure of 10-40 MPa, preferably 20-30 MPa, to obtain fatty alcohols. The reactor discharge product is cooled and separated into recycled hydrogen and liquid crude fatty alcohol. Part of the fatty alcohol is recycled to the previous esterification reaction step.

In the third step alpha-olefins are produced from the obtained fatty alcohols by an endothermic dehydration reaction. The fatty alcohols obtained in the second step are dehydrated to alpha-olefins in a reactor under a pressure of 0-10, preferably 0.01-0.5 MPa and at a temperature of 250-400° C. temperature, preferably 280-330° C. in the presence of a catalyst selected from activated alumina catalysts, gamma-alumina catalysts, theta-alumina catalysts and catalysts comprising zirconium oxide on aluminium oxide. Preferably the catalyst is zirconium oxide on gamma-alumina. The alumina catalysts may additionally comprise alkali metals or alkali earth metals in order to increase the yield of alpha-olefin. The dehydration reactor is either a batch reactor or a fixed bed reactor, preferably a fixed bed reactor. In the fixed bed reactor the liquid hourly space velocity (LHSV) is 0.5-5 $m^3$ of liquid per h/$m^3$ of catalyst, preferably 0.5-2 $h^{-1}$. The product of the third step is mainly alpha-olefin with the carbon number according to the chain length distribution of the fatty alcohol feedstock.

In the fourth step the alpha-olefins obtained in the third step are oligomerised in a reactor at a reaction temperature of 25-300° C. and preferably 50-200° C. and under a pressure from about 0.01 to about 10 MPa, preferably from about 0.01 to about 2 MPa in the presence of an oligomerisation catalyst comprising a heterogeneous or homogeneous catalyst. The required pressure maybe maintained by inert gas pressurization, preferably with nitrogen. Higher oligomerization temperatures typically produce the lower viscosity oligomer products while lower temperatures tend to produce the higher viscosity products. Thus, the viscosity of the oligomer product will depend upon the temperature used in the oligomerization process.

The oligomerization reaction may be carried out in a slurry reactor with the catalyst loading varying from 0.1 to 15 wt-% of the reaction mixture. A lower catalyst charge may cause longer reaction times and a higher catalyst charge may be uneconomical to run, causing filter plugging during the catalyst removal step. Preferably, the catalyst charge is about 0.2 wt-% to about 10 wt-%. Typical reaction times are from about 0.5 to about 100 hours, preferably from about 1 to about 50 hours in a batch reactor. The reaction time is dependent on temperature and the amount of catalyst used in the process. Generally, higher reaction temperatures and a higher catalyst charge promote faster reaction rates. At the end of the run the product is isolated by filtration to remove the catalyst.

The oligomerization reaction may also be carried out in a fixed-bed reactor where the catalyst is in pellet or extruded form and packed in a tubular reactor heated to a desirable temperature. In a fixed bed type operation, the feed may be introduced at from about 0.1 g/g of catalyst/h to about 20 g/g of catalyst/h. Preferred rates are from 0.2 g/g of catalyst/h to about 10 g/g of catalyst/h. Furthermore, the used catalyst may be reused. If the catalyst is aged, e.g., by coke formation during the reaction, it may be regenerated by heat treatment in air or in nitrogen at 500° C. or higher.

The heterogeneous catalyst comprises acidic microporous or mesoporous catalyst material suitable for olefin oligomerization. Preferably the catalyst material is selected from mesoporous materials, zeolites and mixtures thereof, particularly preferably mesoporous materials.

Microporous materials can be zeolites having the pores above 0.5 nm diameter, having a specific surface area between 200-600 $m^2/g$. Examples of zeolites useful in the present invention include ZSM-3, ZSM-4, ZSM-18, ZSM-20, ZSM-38, ZSM-50, mordenite, zeolite Y, and zeolite Beta. Preferably, zeolites are large pore zeolites, particularly preferable zeolites in the group of large pore zeolites are Y or beta-zeolites. In addition, layered zeolites with pore openings formed by 10-membered oxygen rings may also be used in the present invention. Examples of such zeolites include MCM-36, MCM-22, MCM-49 and MCM-56.

Mesoporous catalyst materials can be amorphous materials with regularly arranged, uniform mesopores (2 nm to 50 nm in diameter). Mesoporous catalyst materials can also have irregular mesoporous framework. They have specific surface area above 300 $m^2/g$. An example of the acidic mesoporous materials with regular arranged mesopores that may be used in the present invention includes MCM-41. An example of the acidic mesoporous materials with irregular mesopores includes amorphous silica-alumina. The mesoporous material can also be acidic clay. An example of acidic clay is calcium montmorillonite.

The catalysts are typically in proton form. The catalysts can be converted to the proton form by various conventional methods like ammonium ion exchange and calcination or acid washing. The catalysts may also comprise a carrier for increasing the mechanical stability and formability of the materials. The carrier is typically an inorganic oxide like alumina or silica, preferably the carrier is alumina.

Also homogeneous cationic catalysts, such as $BF_3$ or $AlCl_3$ may be used in the oligomerisation of alpha-olefins, at temperatures of −10-150° C., preferably 40-80° C. It is preferable to use a solid and regenerable catalyst, which can be separated easily from product and regenerated for reuse.

Unreacted monomers are typically removed from the oligomer mixture, suitably by distillation and they may be recycled or reused in the oligomerisation step. After removing of the monomers, for example by stripping, the oligomer mixture comprises dimers, trimers, tetramers and other higher oligomers of the starting olefin or olefin mixture. Depending on the desired application of the polyalpha-olefins, certain polyalpha-olefins, such as dimers may be preferred and they may be isolated through distillation. In this case the product comprises mainly the dimmer product. Under the oligomerisation conditions almost all of the feed monomers are converted to branched monomer compounds, which after subsequent hydrogenation may be used as diesel fuel components, thus giving more economic value for the process of invention.

In the fifth step the oligomers obtained in the fourth step are hydrogenated in a batch hydrogenation reactor using conventional hydrogenation methods, in the presence of hydrogenation catalyst such as palladium on carbon catalysts, nickel on Kieselguhr catalysts, or other known hydrofinishing catalysts. Hydrogenation conditions include temperatures of from about 25° C. to about 400° C. Preferably nickel on Kieselguhr catalysts are used at temperatures from about 150° C. to about 200° C. and palladium on carbon catalyst at temperatures from about 100° C. to about 200° C. In both cases hydrogen pressure of about 0.01 to about 10 MPa, preferably 1-3 MPa is applied.

The Product

The process according to the present invention provides a product, where the chemical structure of the hydrogenated dimer is:

R'—CH($R_a$)—CH($R_b$)—R", wherein each of R', R", $R_a$, and $R_b$ is an alkyl group having from about 1 to about 28 carbon atoms, typically from 1 to about 16 carbon atoms. The alkyl group may be either linear or branched. Preferably the total carbon number of the product ranges between 16 and 52, particularly preferably between 26 and 50.

One skilled in the art will recognize that the total number of carbons in the dimer or co-dimer will be twice the number of carbon atoms in the starting monomer or monomers or their sum.

For comparison, the processes of the state of the art provide oligomeric products, where the chemical structure of the hydrogenated dimer is either:

A) R'—CH($CH_3$)—R" when produced by cationic oligomerization using traditional carbocation mechanism, wherein R' and R" is an alkyl group having from about 7 to about 27 carbon atoms (U.S. Pat. No. 4,282,392); or B) R'—CH($R_a$)—($CH_2$)$_z$—CH($R_b$)—R" when obtained by crystalline acidic catalyst, wherein each of R', R", $R_a$, and $R_b$ is an alkyl group having from about 1 to about 28 carbon atoms, typically from 1 to about 16 carbon atoms; and z is an integer from about 1 to about 10 (U.S. Pat. No. 6,703,356).

The structure A) has high pour point if monomers of carbon number 12 or above are used. The structure B) is more branched, and the pour point is therefore lower.

In the process according to the present invention the solid, acidic oligomerization catalyst effects double bond isomerization of the alpha-olefin feed to form sort of internal olefins. In oligomerization the formed internal olefins form the beneficial branched structure, which in turn lead to low pour points. In addition, some monocycloparaffinic structures are formed as well as branched chain structures.

An oligomeric liquid polyalpha-olefin product is obtained containing dimers and/or co-dimers more than 50 wt-%, and preferably more than 80 wt-%.

The oligomeric liquid polyalpha-olefin product may also comprise higher oligomers (or co-oligomers) such as trimers of the starting olefins, typically about 10 to about 30 wt-% of trimers and about 0 to about 10 wt-% tetramers or higher.

The oligomeric liquid product comprises preferably C26-C50 hydrocarbons and has a pour point below −15° C. The viscosity index of the product is higher than 120. Particularly, the oligomer products with high dimer and/or trimer contents typically have low viscosities and they may be used in formulations for wide-cross grade engine lubricants.

On the other hand, the oligomer products with high tetramer and/or pentamer contents typically have higher viscosity and they may be used in industrial oils as well as engine oils.

The distribution of the saturated hydrocarbons, such as n-paraffins, isoparaffins and cycloparaffins in base oils of this invention is determined by field ionization mass spectroscopy (FIMS). FIMS classifies saturated hydrocarbons according to their carbon and hydrogen atoms in the following groups:

| 1 | $C(n) \cdot H(2n+2)$ | PARAFFINS |
|---|---|---|
| 2 | $C(n) \cdot H(2n)$ | MONOCYCLOPARAFFINS |
| 3 | $C(n) \cdot H(2n-2)$ | DICYCLOPARAFFINS |
| 4 | $C(n) \cdot H(2n-4)$ | TRICYCLOPARAFFINS |
| 5 | $C(n) \cdot H(2n-6)$ | TETRACYCLOPARAFFINS |
| 6 | $C(n) \cdot H(2n-8)$ | PENTACYCLOPARAFFINS. |

The product comprises sufficient branching and monocycloparaffins to yield low pour and cloud points, but also sufficient linear paraffinic character to maintain a relatively high viscosity index. The product may also be used as unconventional base oil, having viscosity indices much higher than those commonly used in the industry.

The oligomers according to the invention exhibit excellent viscosity indices of greater than about 120, more preferably greater than about 130 (ASTM D445). Typically, the viscosity index ranges from about 120 to about 140.

Typically, the oligomers of the present invention have viscosities at 100° C. (ASTM D445) ranging from about 3 mm$^2$/s to about 10 mm$^2$/s, more preferably from about 4 mm$^2$/s to about 8 mm$^2$/s.

As demonstrated in Table 2 and in the examples, the oligomers also maintain low volatility compared to the oligomers of the state of the art in the same viscosity range. Typically, polyalpha-olefins of the state of the art have Noack volatility ranging from about 2 to about 25 wt-%. The volatility is bound to the kinematic viscosity: The lower the viscosity the higher the volatility. The oligomer of the present invention typically has a Noack volatility of below about 15 wt-%, more preferably below about 10 wt-%.

The branched, saturated hydrocarbon product of the present invention contains paraffins more than 80 vol-%, typically more than 99 vol-%.

The branched, saturated hydrocarbon product of the present invention contains cycloparaffins i.e. naphtenes: typically mononaphtenes about 10-40 wt-% and dinaphtenes about 1-10 wt-%, preferably the naphtenes are not multicycloparaffins.

The branched, saturated hydrocarbon product contains aromatics less than 1 vol-%, typically less than 0.2 vol-% according to method IP-391.

Base oil or base oil component according to the invention, manufactured from renewable sources contain $^{14}$C-isotope, which can be used as an evidence of the bio origin of the base oil. The typical $^{14}$C content of the branched, saturated hydrocarbon product is 100%, based on radio-carbon content compared to radio-carbon content of air in the year 1950.

By careful selection of the starting material, reaction conditions, and catalysts, the properties of the resulting oligomers may be controlled. It is also preferable to adjust the molecular size of the intermediate olefins in a way that the lightest dimers have more than about 26 carbon atoms in the final product. The size of the intermediate olefins also has influence on the kinematic viscosity of the oligomerised dimers, trimers and so on. The higher carbon number monomers tend to oligomerise to higher viscosity products and low carbon number monomers to low viscosity products.

The resulting product comprises hydrocarbons in the lubricating base stock range, which can optionally be further processed. The product can be combined with various additives known in the art to provide a finished lubricating oil composition. The hydrogenated oligomers may be used as the sole base stock or blended with other base stocks. The resultant hydrogenated oligomers may be used in high performance functional fluids such as automotive crankcase lubricants, various engine lubricants, and as industrial lubricants.

Advantages

The process according to the invention has several advantages. With the process, a branched, saturated hydrocarbon product suitable for base oil is obtained from renewable sources, which can be determined from its $^{14}$C isotope content. Such base oils originating from biological material have significant environmental benefits in terms of decreased global warming impacts, reduced emissions, and a positive impact on agriculture.

A major trend in passenger car engine oil usage is the extension of oil drain intervals. Thus, a need exists for low viscosity PAO's which exhibit low Noack volatility in order to diminish the loss of engine oil during use. In the processes according to the state of the art 1-decene or 1-dodecene or their mixtures are oligomerised, followed by distillation of the reaction mixture to remove unreacted monomeric and dimeric species. The resulting product is then hydrogenated to saturate the oligomers and a hydrogenated product is obtained having a viscosity of about 5 mm$^2$/s. The product is distilled to provide PAO's of varying viscosity grades. The 4 mm$^2$/s PAO is comprised mostly of trimers and tetramers, while the 6 mm$^2$/s product is comprised of trimers, tetramers, and pentamers.

Properties of a particular grade of PAO are greatly dependent on the alpha-olefin used to make that product. The typical products consist of PAO 2, PAO 4, PAO 6 and PAO 8 based on C$_{10}$ alpha olefins, and PAO 2.5, PAO 5, PAO 7 and PAO 9 based on C$_{12}$ alpha olefins. In general, higher carbon number of the alpha-olefin results in lower Noack volatility and higher pour point of the product. PAO's having a viscosity of 4 mm$^2$/s are typically made from 1-decene and have a Noack volatility of 13-14% and pour point of <−60° C. PAO's having a viscosity of 6 mm$^2$/s are typically prepared from 1-decene or a blend of α-olefins and have a Noack volatility of about 7.0% and pour point of about −60° C.

As shown in Table 2 below, the PAOs produced according to the present invention have lower or equal Noack volatilities compared to the PAOs produced according to the known techniques. In addition, base oils with a low kinematic viscosity of about 4 mm$^2$/s can be achieved by the process of invention, while by the known processes about 5 mm$^2$/s PAO oligomers can be produced from C16 alpha-olefins and about 4 mm$^2$/s PIO oligomers can be produced from C16 internal olefins.

TABLE 2

Typical properties of Group IV and Group VI base oils

| Base oil | Feed %* and C number** | KV100 mm²/s | VI | Noack volatility wt-% | Pour Point ° C. |
|---|---|---|---|---|---|
| Reference 1 | 100 C10 | 3.9 | 124 | 13.0 | −73 |
| Reference 2 | 100 C10 | 4.10 | 122 | 13.5 | <−60 |
| Reference 3 | 100 C10 | 4.0 | 123 | 13.5 | −69 |
| Reference 4 | 50C10:50C12 | 4.15 | 134 | 9.9 | −60 |
| Reference 5 | PIO | 4.3 | 121 | 13.4 | −48 |
| Invention 1 | 100 C16 | 4.3 | 121 | 9.3 | −39 |
| Reference 5 | 100 C10 | 5.05 | 135 | 8.9 | <−56 |
| Reference 6 | 50C10:50C12 | 5.00 | 140 | 6.4 | — |
| Reference 7 | 100 C12 | 5.25 | 148 | 4.8 | −45 |
| Reference 8 | 100 C12 | 5.20 | 145 | 5.5 | −50 |
| Reference 9 | 100 C16 | 4.47 | 123 | 7.5 | −35 |
| Reference 10 | 100 C16 | 5.33 | 130 | 8.3 | −37 |
| Reference 11 | 100 C16 | 5.57 | 129 | 6.9 | −36 |
| Reference 12 | 100 C10 | 5.9 | 138 | 6.8 | −59 |
| Reference 13 | 100 C10 | 5.8 | 135 | 6.5 | −61 |
| Reference 14 | 100 C10 | 5.8 | 138 | 6.5 | −63 |
| Reference 15 | 50C10:50C12 | 5.86 | 143 | 4.3 | — |
| Reference 16 | 100 C12 | 6.20 | 146 | 4.0 | −42 |
| Reference 17 | 100 C12 | 7.0 | 145 | 2.3 | −43 |
| Reference 18 | PIO | 5.8 | 132 | 9.2 | −45 |
| Invention 2 | 100 C16 | 6.7 | 139 | 3.7 | −30 |
| Reference 19 | 100:0 | 7.9 | 137 | 3.2 | −60 |
| Reference 20 | 100:0 | 7.8 | 138 | 3.0 | −60 |

*= Feed % means percentage of the feed olefin in process,
**= C number means the carbon number of the feed olefin.

Invention 1 and 2 are products obtained from the process described in Example 4. Reference products 1-20 in different viscosity ranges are commercially available PAO and PIO base oil products.

The base oil or base oil component according to the invention has high viscosity index, which leads to a significantly decreased need of high price Viscosity Index Improver (VII) or in other terms Viscosity Modifier (VM). It is commonly known, that the VII is an additive, which causes highest amount of deposits in vehicle engines.

The branched, saturated hydrocarbon product contains no sulphur. Thus, in the pre-treatment of exhaust gases, the catalysts and particulate filters can easily be adjusted to the sulphur-free fuel together with lubricating oil manufactured using the hydrocarbon compound according to invention. Catalyst poisoning is reduced and catalyst service lifetime is significantly prolonged. Also, because the base oil or base oil component is non-toxic, contains no sulphur, nitrogen or aromatic compounds typically present in the conventional mineral oil based products, it may more safely be used in applications where the end user is exposed to oil or oil spray.

The obtained base oil or base oil component contains no petroleum. Due to the non-polar nature of the base oil, it may be blended with other hydrocarbon base oils. Further, it is compatible with elastomers, and thus it can be used in modern vehicle engines without modifications.

The response of the base oil or base oil component according to the invention is extremely high for antioxidants and pour point depressants, and thus the life time of the lubricating oils are longer and they can be used in the colder environment than lubricants based on the conventional base oils.

Branching in the paraffinic carbon chain enhances low temperature properties, such as pour point, cold filter plugging point and viscometric properties under low temperature and high shear, or in other words low temperature cranking viscosity. The extremely good low temperature properties make it possible to use the branched, saturated hydrocarbon product as base oil or base oil component also in the arctic environment.

The cycloparaffins in the base oil or base oil component obtained by the process of invention are monocycloparaffins i.e. mononaphtenes. It is commonly known that mononaphtenes are relatively good base oil compounds due to their low pour point and good viscosity index. In addition, the monocycloparaffinic structures in the base oil enhance additive solubility. This is advantageous since in the finished lubricants, several additives, such as viscosity modifiers, detergents, dispersants, rust inhibitors, anti-wear additives, antioxidants, extreme pressure additives, friction modifiers, pour point or cloud point depressants, demulsifiers, corrosion inhibitors, and foam inhibitors may be added to further enhance the performance of the product.

Even though the branched, saturated hydrocarbon product is produced from saturated and unsaturated natural fatty acids, it contains no oxygen, and thus its hydrolytic stability is much higher than that of synthetic ester base oils. Due to the lack of ester bonds, also the formation of acidic degradation products is minimized. In addition, the oxidation stability of the saturated base oil or base oil component is higher than that of ester base oil containing unsaturated fatty acid structural units.

An additional advantage of the base oil or base oil component according to this invention is that it fulfils the API group IV base oil specifications. Therefore it can be used in engine oil formulations like other group IV base oils according the same interchanging rules without need to perform new engine tests.

The lubricating base oil manufacturing plants are typically integrated to crude oil refineries or Fischer-Tropsh synthesis plants, producing paraffinic wax for feed. Instead, now there is no need to integrate the manufacturing plants of this invention to refineries in the traditional manner, thereby easing the demand for 1-decene and other crude oil based olefins as a feedstock and enabling the use of higher olefins of bio-origin as new starting materials for polyolefin manufacture. In addition, the prices of biological feeds are remarkably lower than those of synthetic feeds.

The following examples illustrate the process according to the invention with some preferable embodiments and provide physical properties of typical products. Also, the examples demonstrate the advantages of using the process of invention to produce base stock with a high VI, low pour point, and low volatility from alpha-olefins from biological origin. However, it is evident to a person skilled in the art that the scope of the invention is not meant to be limited to these examples.

EXAMPLES

Example 1

Manufacture of Alpha-Olefins from Fatty Acids

Alpha-olefins were produced from distilled C16 fatty acid feed. The alpha-olefins were prepared by feeding 200 g fatty acids together with 1.5 molar excess of C16 fatty alcohol to an autoclave under stirring to form a wax ester through esterification reaction. Esterification took place under atmospheric pressure at a temperature of 250° C. Reaction time was 3 hours. No catalyst was used. Water liberated in the reaction was purged with nitrogen flow of 6 l/h.

The obtained wax ester and hydrogen were thereafter charged to the fixed bed hydrogenation reactor, where they were brought in contact with a copper-chromite catalyst at 230° C. and 30 MPa pressure, forming C16 fatty alcohols. The product was cooled and the liquid crude fatty alcohol was separated. A part of this prepared fatty alcohol was used in esterification.

The fatty alcohol obtained above was dehydrated in a flow reactor with zirconia/gamma-alumina catalyst, wherein zirconia was prepared from zirconium tetrachloride and water on alumina with atomic layer epitaxy method. Fatty alcohol was fed to a reactor kept at 300° C. with weight space velocity of about 6 l/h producing 1-hexadecene.

The alpha-olefin prepared above was suitable as feed in oligomerisation.

Example 2

Oligomerization of Alpha-Olefins in a Batch Reactor 50 g of 1-hexadecene and 2 g of a catalyst were mixed in an autoclave reactor. The catalysts used are shown in Table 3 below. The mixture was heated to 200° C. for 24 hours under nitrogen atmosphere. The pressure was 2.0 MPa. Conversion of the reaction was calculated to all products other than C16.

TABLE 3

1-hexadecene oligomerization

| | Catalyst | | | |
|---|---|---|---|---|
| | Beta 1 | Beta 2 | Y | H-MCM-41 |
| | C16 conversion (%) | | | |
| Product distribution (wt-%): | 62 | 77 | 77 | 74 |
| <C16 | 11 | 11 | 1 | 3 |
| branched C16= | 33 | 20 | 9 | 23 |
| n-C16= | 5 | 3 | 14 | 3 |
| C17-C31 | 17 | 18 | 3 | 6 |
| C32 | 28 | 39 | 61 | 42 |
| C48 | 5 | 8 | 11 | 20 |
| >C48 | 1 | 2 | 1 | 3 |

The catalysts used were Y-zeolite (TOSOH Co.), beta-zeolite 1 (TOSOH Co.) and beta-zeolite 2 (TOSOH Co.), and the mesoporous material MCM-41 was prepared according to Catalysis Letters 36 (1996) 103.

As can be seen in Table 3 a high yield of C32 dimer and C48 trimer is obtained. The C16 monomer residue is mostly branched olefin and after hydrogenation it may suitably be used as a diesel fuel.

Example 3

Oligomerization in a Fixed Bed Reactor 1-hexadecene was fed to a fixed bed tubular reactor with 5 g catalyst diluted with silicon carbide in ratio 1:3. The catalyst used was mesoporous material MCM-41, described in example 2, the aluminium content of which was 2.5 wt-%, amount of acidic sites 150 μmol/g and surface area of mesopores >800 m². The reactor temperature was 200° C., the pressure was 2.0 MPa and the feed rate was 10 g/h. The reaction was followed by GC analysis. In Table 4 the conversion and the composition of oligomerization product is presented at different times on stream.

TABLE 4

1-hexadecene oligomerization in fixed bed reactor

| | TOS (h) (time on stream) | | | | | | | |
|---|---|---|---|---|---|---|---|---|
| Product distribution (wt- | 6 | 24 | 30 | 48 | 54 | 72 | 78 | 96 |
| | | | | C16 conversion (%) | | | | |
| %): | 78 | 71 | 68 | 64 | 61 | 54 | 52 | 47 |
| <C16 | 3 | 2 | 2 | 1 | 1 | 1 | 1 | 1 |
| Branched C16= | 20 | 24 | 24 | 24 | 23 | 24 | 23 | 21 |
| n-C16= | 2 | 5 | 8 | 12 | 16 | 22 | 25 | 32 |
| C17-C31 | 5 | 2 | 1 | 1 | 1 | 1 | 1 | 1 |
| C32 | 43 | 51 | 51 | 50 | 49 | 45 | 44 | 40 |
| C48 | 21 | 15 | 14 | 11 | 10 | 7 | 6 | 5 |
| >C48 | 6 | 1 | 0 | 1 | 0 | 0 | 0 | 0 |

Example 4

Hydrogenation of Oligomer Product and Properties of the Base Oil Component

The oligomer product from the fixed bed oligomerization in example 3 was distilled to isolate the monomer fraction, the hexadecene dimer fraction and the higher oligomer portion. The dimer and heavier fractions were then hydrogenated in separate batches at 200° C. and 5 MPa hydrogen pressure using a heterogeneous nickel oxide catalyst. The reaction time was 2 h. The properties of the obtained products are summarized in Table 5. Base oils with excellent low Noack volatility, pour points and good viscosity indexes were obtained.

TABLE 5

Properties of the base oils according to the invention

| Analysis | C16 dimer | C16 > dimer | Method |
|---|---|---|---|
| KV100 (mm²/s) | 4.3 | 6.7 | ASTM D445 |
| KV40 (mm²/s) | 20.2 | 37.2 | ASTM D445 |
| VI | 121 | 139 | ASTM D2270 |
| Pour point (° C.) | −39 | −30 | ASTM D97 |
| Volatility Noack (wt-%) | 9.3 | 3.7 | CECL-40-93-B |
| Molecular distribution (wt-%) | | | |
| Aromatics | <0.02 | 0.18 | ASTM D2549 |
| Paraffins | 63.6 | 50.0 | FI-MS |
| Mononaphtenes | 33.3 | 36.6 | FI-MS |
| Dinaphtenes | 3.3 | 9.5 | FI-MS |
| Other naphtenes | 0.4 | 5.0 | FI-MS |

The invention claimed is:

1. A process for the manufacture of branched saturated hydrocarbons, which comprises:
   a first step of forming an ester of a feedstock comprising at least one fatty acid and at least one fatty alcohol;
   a second step of hydrogenating the obtained ester from the first step to form a fatty alcohol;
   a third step of dehydrating the obtained fatty alcohol from the second step to form an alpha-olefin;
   a fourth step of oligomerising the alpha-olefin from the third step to form an oligomer; and
   a fifth step of hydrogenating the oligomer from the fourth step to form branched saturated hydrocarbons.

2. The process according to claim 1, wherein the fatty acid has a total carbon number of 8 to 26.

3. The process according to claim 1, wherein the feedstock originates from biological raw materials.

4. The process according to claim 1, wherein in the first step at least one fatty acid is esterified under 0-0.1 MPa pressure and at a temperature of 120-320° C., together with 1-2 molar excess of fatty alcohol having total carbon number of 8 to 26.

5. The process according to claim 1, wherein in the second step the ester is hydrogenated to a fatty alcohol in the presence of hydrogen at a temperature of 100-350° C. and under a pressure of 10-40 MPa, in the presence of a hydrogenation catalyst selected from the group consisting of copper catalysts and copper-chromite catalysts.

6. The process according to claim 1, wherein a portion of the fatty alcohol obtained in the second step is recycled to the first step.

7. The process according to claim 1, wherein in the third step the fatty alcohol obtained in the second step is dehydrated to an alpha-olefin in the presence of a catalyst selected from the group consisting of activated alumina catalysts, gamma-alumina catalysts, theta-alumina catalysts and catalysts comprising zirconium oxide on aluminium oxide, under a pressure of 0-10 MPa and at a temperature of 250-400° C.

8. The process according to claim 1, wherein in the fourth step, the alpha-olefin is oligomerised at a temperature of 25-300° C. and under a pressure from about 0.01 to about 10 MPa in the presence of a heterogeneous or homogeneous oligomersation catalyst.

9. The process according to claim 8, wherein the oligomerisation catalyst is an acidic microporous or mesoporous catalyst.

10. The process according to claim 1, wherein in the fifth step the oligomer is hydrogenated in the presence of a hydrogenation catalyst selected from the group consisting of palladium on carbon catalysts, nickel on Kieselguhr catalysts and hydrofinishing catalysts, at a temperature of 25-400° C., and under hydrogen pressure of 0.01-10 MPa.

11. The process according to claim 1, wherein the manufactured branched saturated hydrocarbons are a base oil or base oil component.

12. The process according to claim 1, wherein the manufactured branched saturated hydrocarbons are polyalpha-olefins.

13. The process according to claim 1, wherein the fatty acid has a total carbon number of 12 to 20.

14. The process according to claim 13, wherein in the first step at least one fatty acid is esterified under 0-0.1 MPa pressure and at a temperature of 120-320° C., together with 1-2 molar excess of fatty alcohol having total carbon number of 12 to 20.

15. The process according to claim 14, wherein in the second step the ester is hydrogenated to a fatty alcohol in the presence of hydrogen at a temperature of 100-350° C. and under a pressure of 10-40 MPa, in the presence of a hydrogenation catalyst selected from the group consisting of copper catalysts and copper-chromite catalysts.

16. The process according claim 15, wherein in the third step the fatty alcohol obtained in the second step is dehydrated to an alpha-olefin in the presence of a catalyst selected from the group consisting of activated alumina catalysts, gamma-alumina catalysts, theta-alumina catalysts and catalysts comprising zirconium oxide on aluminium oxide, under a pressure of 0-10 MPa and at a temperature of 250-400° C.

17. The process according to claim 16, wherein in the fourth step, the alpha-olefin is oligomerised at a temperature of 25-300° C. and under a pressure from about 0.01 to about 10 MPa in the presence of a heterogeneous or homogeneous oligomersation catalyst.

18. The process according to claim 17, wherein in the fifth step the oligomer is hydrogenated in the presence of a hydrogenation catalyst selected from the group consisting of palladium on carbon catalysts, nickel on Kieselguhr catalysts and hydrofinishing catalysts, at a temperature of 25-400° C., and under hydrogen pressure of 0.01-10 MPa.

* * * * *